(12) United States Patent
Chen

(10) Patent No.: US 8,226,946 B2
(45) Date of Patent: *Jul. 24, 2012

(54) ENHANCEMENT OF LIGHT ACTIVATED THERAPY BY IMMUNE AUGMENTATION USING ANTI-CTLA-4 ANTIBODY

(75) Inventor: James Chen, Clyde Hill, WA (US)

(73) Assignee: Light Sciences Oncology, Inc., Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/154,156

(22) Filed: Jun. 6, 2011

(65) Prior Publication Data

US 2011/0236402 A1 Sep. 29, 2011

Related U.S. Application Data

(63) Continuation of application No. 12/537,139, filed on Aug. 6, 2009, now Pat. No. 7,993,640.

(60) Provisional application No. 61/086,597, filed on Aug. 6, 2008.

(51) Int. Cl.
  *A61K 39/395* (2006.01)
(52) U.S. Cl. .................................................. 424/130.1
(58) Field of Classification Search .................. None
  See application file for complete search history.

(56) References Cited

U.S. PATENT DOCUMENTS

| | | | |
|---|---|---|---|
| 4,128,173 A | 12/1978 | Lazarus et al. | |
| 4,408,263 A | 10/1983 | Sternlicht | |
| 4,522,302 A | 6/1985 | Paikoff | |
| 5,445,608 A | 8/1995 | Chen et al. | |
| 5,634,921 A | 6/1997 | Hood et al. | |
| 5,814,008 A | 9/1998 | Chen et al. | |
| 5,851,221 A | 12/1998 | Rieder et al. | |
| 5,865,840 A | 2/1999 | Chen | |
| 6,162,214 A | 12/2000 | Mueller et al. | |
| 6,210,425 B1 | 4/2001 | Chen | |
| 6,240,925 B1 | 6/2001 | McMillan et al. | |
| 6,273,904 B1 | 8/2001 | Chen et al. | |
| 6,350,772 B1 | 2/2002 | Kuroiwa et al. | |
| 6,416,531 B2 | 7/2002 | Chen | |
| 6,445,011 B1 | 9/2002 | Hirano et al. | |
| 6,454,789 B1 | 9/2002 | Chen et al. | |
| 6,602,274 B1 | 8/2003 | Chen | |
| 6,661,167 B2 | 12/2003 | Eliashevich et al. | |
| 6,689,380 B1 | 2/2004 | Marchitto et al. | |
| 6,784,460 B2 | 8/2004 | Ng et al. | |
| 6,899,723 B2 | 5/2005 | Chen | |
| 6,958,498 B2 | 10/2005 | Shelton et al. | |
| 7,015,240 B2 | 3/2006 | North et al. | |
| 7,993,640 B2 * | 8/2011 | Chen ........................ | 424/130.1 |
| 2001/0049502 A1 | 12/2001 | Chen | |
| 2002/0004053 A1 | 1/2002 | Biel | |
| 2003/0114434 A1 | 6/2003 | Chen et al. | |
| 2004/0122419 A1 | 6/2004 | Neuberger | |
| 2005/0013812 A1 | 1/2005 | Dow et al. | |
| 2005/0113815 A1 | 5/2005 | Ritchie et al. | |
| 2005/0187597 A1 | 8/2005 | Vanderschuit | |
| 2005/0228260 A1 | 10/2005 | Burwell et al. | |
| 2005/0279354 A1 | 12/2005 | Deutsch et al. | |
| 2006/0211639 A1 | 9/2006 | Bratzler et al. | |
| 2006/0265031 A1 | 11/2006 | Skwarek et al. | |
| 2006/0282132 A1 | 12/2006 | Arai et al. | |
| 2011/0008372 A1* | 1/2011 | Chen ........................ | 424/174.1 |

FOREIGN PATENT DOCUMENTS

| | | |
|---|---|---|
| WO | WO-0224199 A1 | 3/2002 |
| WO | WO-03074566 A2 | 9/2003 |
| WO | WO-2006036968 A2 | 4/2006 |

OTHER PUBLICATIONS

Anichini et al., "The paradox of T cell-mediated antitumor immunity in spite of poor clinical outcome in human melanoma," Cancer Immunol Immunother, vol. 53: 855-864, 2004.
Armeanu et al., "Direct and Natural Killer Cell-Mediated Antitumor Effects of Low-Dose Bortezomib in Hepatocellular Carcinoma," Clin Cancer Res, vol. 14, No. 11: 3520-3528, 2008.
Bae et al., "Photodynamic therapy-generated tumor celllysates with CpG-ogliodeoxynucleotide enhance immunotherapy efficacy in human papillomavirus 16 (E6/E7) immortalized tumor cells," Cancer Science, vol. 98, No. 5: 747-752, 2007.
Baecher-Allan et al., "Immune regulation in tumor-bearing hosts." Current Opinion in Immunology, vol. 18: 214-219, 2006.
Benigni et al., "Phenotype and Homing of CD4 Tumor-Specific T Cells is Modulated by Tumor Bulk," The Journal of Immunology, vol. 175: 739-748, 2005.
Bromley et al., "Characterization of an antitumor Immune response after light-activated drug therapy using talaporfin sodium in a spontaneously metastasizing mammary tumor model," ASCO Meeting Abstracts: 2pp, 2009.
Bunt et al., "Tumor-Associated Myeloid-Derived Suppressor Cells," Cancer Immunotherapy, Chapter 17: 309-331, 2007.
Campoli et al., "Tumor-Induced Immune Suppression and Immune Escape," Cancer Drug Discovery and Development: Immunotherapy of Cancer, Ch. 15: 263-284, 2006. Canti et al., "Photodynamic therapy and the immune system in experimental oncology." Photochem. Photobiol. Sci. vol. 1: 79-80, 2002.
Castano et al., "Specific anti-tumor immune response with photodynamic therapy mediated by benzoporphyrin derivative and chlorine (e6)," Proceedings of SPIE, vol. 4961: 1-9, 2003.
Chen et al., "New Technology for Deep Light Distribution in Tissue for Phototherapy," Cancer J, vol. 8: 154-163, 2002.
Coukos et al., "The Tumor Microenvironment," Cancer Drug Discovery and Development: Immunotherapy of Cancer, Ch. 16: 285-301, 2006.
Danna et al., "Surgical Removal of Primary Tumor Reverses Tumor-Induced Immunosuppression Despite the Presence of Metastatic Disease," Cancer Research, vol. 64: 2205-2211, 2004.
Das et al., "Induction of apoptosis and manganese superoxide dismutase gene by photodynamic therapy in cervical carcinoma cell lines," Int J Clin. Oncol, vol. 5:97-103, 2000.

(Continued)

*Primary Examiner* — Ilia Ouspenski
(74) *Attorney, Agent, or Firm* — Perkins Coie LLP

(57) ABSTRACT

The efficacy of light activated therapy treatment is enhanced by stimulating the immune system of the patient substantially above a normal level. Abnormal tissue that is destroyed by the light activated therapy releases factors that stimulate the immune system, leading to systemic reductions in abnormal tissue (i.e., reduction beyond the region treated using light). By further stimulating the immune system using an anti-CTLA-4 antibody, the systemic destruction of abnormal tissue is enhanced.

8 Claims, 1 Drawing Sheet

Figure 1:
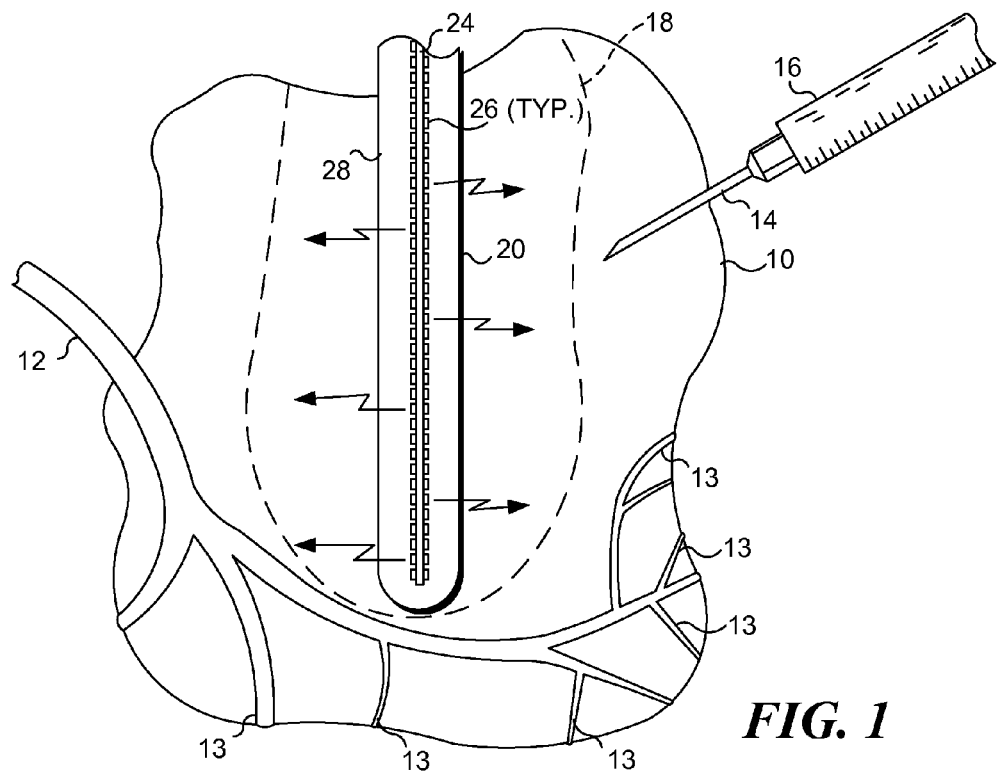

OTHER PUBLICATIONS de Visser et al., "Effects of TGF-? on the immune system: implications for cancer immunotherapy," Leukemia, vol. 13: 1188-1199, 1999.

de Visser, Karin, "Spontaneous immune responses to sporadic tumors: tumor-promoting, tumor-protective or both?" Cancer Immunol Immunother vol. 57: 1531-1539, 2008.

Derhovanessian et al., "Immunity, ageing, and cancer," Immunity & Ageing, vol. 5: 16pp, 2008.

Disis et al., "Use of tumour-responsive T cells as cancer treatment," www.thelancet.com vol. 373: 674-683, 2009.

Emens et al., "Manipulating Immunological Checkpoints to Maximize Antitumor Immunity," Cancer Drug Discovery and Development: Immunotherapy of Cancer, Ch. 19: 331-353, 2006.

Engel et al., "A Phase II Study of Single Agent Bortezomib in Patients with Metastatic Breast Cancer: A Single Institution Experience," Cancer Investigation, vol. 25, No. 8: 733-737, 2007.

Finn, Olivera., "Cancer Immunology," N Engl. J Med, vol. 358, No. 25: 2704-2715, 2008.

Fong et al., "Anti-Cytotoxic T-Lymphocyte Antigen-4 Antibody: The First in an Emerging Class of Immunomodulatory Antibodies for Cancer Treatment," Journal of Clinical Oncology, vol. 26, No. 32: 5275-5283, 2008.

Frumento et al., "Targeting Tumor-Related Immunosuppression for Cancer Immunotherapy," Endocrine, Metabolic, & Immune Disorders—Drug Targets, vol. 6: 223-237, 2006.

Gajewski et al., "Immune resistance orchestrated by the tumor microenvironment," Immunological Reviews, vol. 213: 131-145, 2006.

Gajewski et al., "Immune suppression in the Tumor Microenvironment," J Immunother, vol. 29, No. 3: 233-240, 2006.

Ganss et al., "Overcoming tumor-intrinsic resistance to immune effector function," Eur. J Immunol., vol. 34: 2635-2641, 2004.

Goldszmid et al., "Dendritic Cells Charged with Apoptotic Tumor Cells Induce Long-Lived Protective CD4+ and CD8+ T Cell Immunity against B16 Melonoma," The Journal of Immunology: 5940-5947, 2003.

Gollnick et al., "Generation of Effective Antitumor Vaccines Using Photodynamic Therapy," Cancer Research, vol. 62: 1604-1608, 2002.

Gollnick et al., "Photodynamic Therapy and Anti-Tumor Immunity," Lasers in Surgery and Medicine, vol. 38: 509-515, 2006.

Gollnick et al., "Photodynamic therapy (PDT) control of distant disease through immune mechanisms," Proc Amer Assoc Cancer Res, vol. 45: 2pp, 2004.

Gonzalez et al., "Effect of surgical resection of metastatic disease on immune tolerance to cancer. How a systemic disease could be controlled by a local therapy," Clin Transl Oncol vol. 9: 571-577, 2007.

Gravekamp et al., "Cancer vaccination: Manipulation of immune responses at old age," Mechanisms of Ageing and Development, vol. 130:67-75, 2009.

Gupta, Sudhir., "Molecular mechanisms of apoptosis in the cells of the immune system in human aging," Immunological Reviews vol. 205: 114-129 2005.

Halliday et al., "Spontaneous Regression of Human Melanoma/Nonmelanoma Skin Cancer: Association with Infiltrating CD4+ T Cells," World J Surg., vol. 19: 352-358, 1995.

Hamblin et al., "Combination Immunotherapy and Photodynamic Therapy for Cancer," Proceedings of SPIE, vol. 6087: 12pp, 2006.

Hamblin et al., "Scavenger receptor-targeted photodynamic therapy of 1774 tumors in mice: tumor response and concomitant immunity," Proceedings of SPIE, vol. 4617: 1-10, 2002.

Harvey et al., "Killing tumor cells: the effect of photodynamic therapy using mono-L-aspartyl chlorine and NS-398," The American Journal of Surgery, vol. 189: 302-305, 2005.

Henderson et al., "Choice of Oxygen-Conserving Treatment Regimen Determines the Inflammatory Response and Outcome of Photodynamic Therapy of Tumors," Cancer Research, vol. 64: 2120-2126, 2004.

Igney et al., "Immune escape of tumors: apoptosis resistance and tumor counterattack," Journal of Leukocyte Biology, vol. 71: 907-920, Jun. 2002.

Ishikawa et al., "Perioperative immune responses in cancer patients undergoing digestive surgeries," World Journal of Surgical Oncology, vol. 7, No. 7: 22pp, 2009.

Ito, Takashi, Cellular and Subcellular Mechanisms of Photodynamic Action: The 102 Hypothesis as a Driving Force in Recent Research, Photochemistry and Photobiology. vol. 28: 493-508, 1978.

Jackaman et al., "Deliberately provoking local irflammation drives tumors to become their own protective vaccine site," International Immunology, vol. 20, No. 11: 1467-1479, 2008.

Kabingu et al., "CD8+ T cell-mediated control of distant tumours following local photodynamic therapy is independent of CD4+ T cells and dependent on natural killer cells," British Journal of Cancer: 1-10, 2007.

Kaufman et al., "Immune system versus tumor: shifting the balance in favor of DCs and effective immunity," The Journal of Clinical Investigation, vol. 113, No. 5: 664-667, 2004.

Kessel et al., "Mitochondrial photo damage and PDT -induced apoptosis," Journal of Photochemistry and Photobiology B, vol. 42: 89-95, 1998.

Kim et al., "Cancer Cell Immune Escape and Tumor Progression by Exploitation of Anti-Inflammatory and Pro-Inflammatory Responses," Cancer Biology and Therapy, vol. 4, No. 9: 924-933, 2005.

Kim et al., "Tumor-Driven Evolution of Immunosuppressive Networks during Malignant Progression," Cancer Res, vol. 66, No. 11: 5527-5536, 2006.

Klebanoff et al., "CD8+ T-cell memory in tumor mmunology and immunotherapy," Immunol. Rev., vol. 211: 214-224, 2006.

Korbelik, Mladen., "Advances in the understanding of host response associated with tumor PDT," Biophotonics and Immune Responses II, Proc. of SPIE, vol. 6438: 10pp., 2007.

Korbelik et al., "Interaction Between Photodynarnic Therapy and BCG Immunotherapy Responsible for the Reduced Recurrence of Treated Mouse Tumors," Photochemistry and Photobiology, vol. 73, No. 4: 403-409, 2001.

Korbelik et al., "Photodynamic therapy-generated vaccine for cancer therapy," Cancer Immunol. Immunother., vol. 55: 900-909, 2006.

Korbelik et al., "Photodynamic therapy-generated vaccines: relevance of tumour cell death expression," British Journal of Cancer: 1-7, 2007.

Korbelik et al., "Photodynamic Therapy-Induced Cell Surface Expression and Release of Heat Shock Proteins: Relevance for Tumor Response," Cancer Res., vol. 65, No. 3: 1018-1026, 2005.

Korbelik et al., "Photodynamic Therapy-mediated Immune Response against Subcutaneous Mouse Tumors," Cancer Research, vol. 59: 1941-1946, 1999.

Kujundzic et al., "A Phase II Safety and Effect on Time to Tumor Progression Study of Intratumoral Light Infusion Technology Using Talaporfin Sodium in Patients With Metastatic Colorectal Cancer," Journal of Surgical Oncology: 1-7, 2007.

Lehrnbecher et al., "Changes in host defence induced by malignancies and antineoplastic treatment: implication for immunotherapeutic strategies," Lancet Oncology, vol. 9: 269-278, 2008.

Li et al., "Apoptosis and expression of cytokines triggered by pyropheophorbide-a methyl ester-mediated photodynamic therapy in nasopharyngeal carcinoma cells," Photodiagnosis and Photodynamic Therapy, vol. 3: 247-258, 2006.

Liu et al., "Overcoming Immune Tolerance to Cancer by Heat Shock Protein Vaccines," Molecular Cancer Therapeutics, vol. 1: 1147-1151, 2002.

Lustgarten, Joseph, "Cancer, aging and immunotherapy: lessons learned from animal models," Cancer Immunol. Immunother.: 11pp., 2009.

Lustig et al., "A Multicenter Phase I Safety Study of Intratumoral Photo activation of Talaporfin Sodium in Patients with Refractory Solid Tumors," Cancer, vol. 98, No. 8: 1767-1771, 2003.

Mohebtash et al., "Phase I trial of PSA-TRICOM vaccine and ipilimumab in patients (Pts) with metastatic castrate-resistant prostrate cancer (mCRPC)," Genitourinary Cancers Symposium: Abstract only 3pp, 2009.

Molhoek et al., "Apoptosis of CD4+CD25high T cells in response to Sirolimus requires activation of T cell receptor and is modulated by IL-2," Cancer Immunol Immunother., vol. 58: 867-876, 2009.

Morton et al., "Cytoreductive Surgery and Adjuvant Immunotherapy: A New Management Paradigm for Metastatic Melanoma " CA Cancer J Clin vol. 49, No. 2: 101-116, 1999.

Mozaffari et al., "NK-cell and T-cell functions in patients with breast cancer: effects of surgery and adjuvant chemo- and radiotherapy," British Journal of Cancer, vol. 97: 105-111, 2007.

Myrianthefs et al., "Cancer cachexia and immunomodulation," Journal of BUON, vol. 10: 181-188, 2005.

Nigam et al., "Immunomodulatory properties of antineoplastic drugs administered in conjunction with GM-CSF-secreting cancer cell vaccines," International Journal of Oncology, vol. 12: 161-170, 1998.

Nowis et al., "The influence of photodynamic therapy on the immune response," Photodiagnosis and Photodynamic Therapy, vol. 2: 283-298 2005.

Nylandsted et al., "Selective depletion of heat shock protein 70 (Hsp70) activates a tumor-specific death program that is independent of caspases and bypasses Bcl-2," PNAS, vol. 97, No. 14: 7871-7876, 2000.

Ochsenbein, Adrian, "Principles of tumor immunosurveillance and implications for immunotherapy," Cancer Gene Therapy, vol. 9: 1043-1055, 2002.

Oseroff, Alan, "PDT as a Cytotoxic Agent and Biological Response Modifier: Implications for Cancer Prevention and Treatment in Immunosuppressed and Immunocompetent Patients," Journal of Investigative Dermatology, vol. 126: 542-544, 2006.

Pilling et al., "Prolonged Survival Due to Spontaneous Regression and Surgical Excision of Malignant Mesothelioma," The Society of Thoracic Surgeons, vol. 83: 314-315, 2007.

Pockley, A. Graham., "Heat shock proteins as regulators of the immune response," The Lancet, vol. 362: 469-476, 2003.

Preise et al., "Systemic antitumor protection by vascular-targeted photodynamic therapy involves cellular and humoral immunity," Cancer Immunol. Immunother, vol. 58: 71-84, 2009.

Prendergast, George, "Breaking Immune Suppression in Cancer: The Emerging Revolution in Immunotherapy." Cancer Reviews Online, vol. 7: 13-14, 2007.

Printz, Carrie, "Spontaneous Regression of Melanoma May Offer Insight Into Cancer Immunology," JNCI Journal of the National Cancer Institute, vol. 93, No. 14: 1047-1048, 2001.

Rabinovich et al., "Programmed Death Ligand-I and Galectin-I: Pieces in the Puzzle of Tumor-Immune Escape," Cancer Immunotherapy, Chapter 18: 333-346, 2007.

Salazar et al., "Cancer Vaccines: The Role of Tumor Burden in Tipping the Scale Towards Vaccine Efficacy," Journal of Clinical Oncology, vol. 23, No. 30: 7397-7398, 2005.

Schmid et al., "A phase IIII study of bortezomib and capecitabine in patients with metastatic breast cancer previously treated with taxanes and/or anthracyclines," Annals of Oncology, vol. 19:871-876, 2008.

Schumacher et al., "Immunosensitization of Tumor Cells to Dendritic Cell Activated Immune Responses with the Proteasome Inhibitor Bortezomib (PS-341, Velcade)," The Journal of Immunology, vol. 176: 4757-4765, 2006.

Smyth et al., "CD4+CD25+ T Regulatory Cells Suppress NK Cell-Mediated Immunotherapy of Cancer," The Journal of Immunology, vol. 176: 1582-1587, 2006.

Spiesek et al., "Bortezomib enhances dendritic cell (DC)-mediated induction of immunity to human myeloma via exposure of cell surface heat shock protein 90 on dying tumor cells: therapeutic implications," Immunobiology, vol. 109, No. 11: 4839-4845, 2007.

Staal et al., "The Marriage of Growth Factor Inhibitors and Chemotherapy: Bliss or Bust?" Journal of Clinical Oncology, vol. 27, No. 10: 1545-1548, 2009.

Stewart et al., "Altered Immune Function during Long-Term Host-Tumor Interactions Can Be Modulated to Retard Autochthonous Neoplastic Growth," The Journal of Immunology: 2851-2859, 2007.

Stewart et al., "Immunological responses can have both pro-and antitumour effects: implications for immunotherapy," Expert Reviews in Molecular Medicine, vol. 9, Issue 4: 1-20, 2007.

Stoll, Basil A., "Spontaneous regression of cancer: new insights," Biotherapy, vol. 4: 23-30, 1992.

Tapia et al., "Activity of bortezomib, a proteasome inhibitor, in breast cancer cells: association with negative estrogen receptor and IKKINF-?B expression," ASCO Annual Meeting Abstracts: 3pp., 2005.

Thirumaran et al., "Cytotoxic Chemotherapy in Clinical Treatment of Cancer," Cancer Immunotherapy, Chapter 7: 101-116, 2007.

Thong et al., "Immune Response Against Angiosarcoma Following Lower Fluence Rate Clinical Photodynamic Therapy," Journal of Environmental Pathology, Toxicology, and Oncology, vol. 27, No. 1: 43-50, 2008.

Thong et al., "Photodynamic-therapy-activated immune response against distant untreated tumours in recurrent angiosarcoma,." Lancet Oncolgy, vol. 8: 950-952, 2007.

Valenti et al., "Tumor-Released Microvesicles as Vehicles of Immunosuppression," Cancer Res., vol. 67, No. 7: 2912-2915, 2007.

van Duijnhoven et al., "The immunological consequences of photodynamic treatment of cancer, a literature review." Immunobiology, vol. 207: 105-113, 2003.

Waldmann, Thomas, "Effective Cancer Therapy Through Immunomodulation," Annu. Rev. Med., vol. 57: 65-81, 2006.

Wang et al., "A phase IIII safety and efficacy study of intra tumoral light-activated drug therapy using talaporfin sodium in patients with inoperable hepatocellular carcinoma," ANSO Annual Meeting Abstracts: 2pp, 2009.

Wang, Rong-fu., "Regulatory T Cells in Tumor Immunity: Role of Toll-Like Receptors," Cancer Immunotherapy, Chapter 15: 277-287, 2007.

Whiteside, Theresa, "The Role of Immune Cells in the Tumor Microenvironment," Cancer Treatment and Research, vol. 130, Chapter 5: 103-124, 2006.

Widen et al., "Overcoming immunosuppressive mechanisms," Annals of Oncology, vol. 19, Supplement 7: vii241-vii247, 2008.

Wojtowicz-Praga, Slawomir., "Reversal of Tumor-Induced Immunosuppression: A New Approach to Cancer Therapy," Journal of Immunotherapy, vol. 20, No. 3: 165-177, 1997.

Yakirevich et al., "Regulatory T Lymphocytes: Pivotal Components of the Host Antitumor Response," Journal of Clinical Oncology, vol. 25, No. 18: 2506-2508, 2007.

Yang et al., "Bortezomib (VEL CAD E) in metastatic breast cancer: pharmacodynamics, biological effects, and prediction of clinical benefits," Annals of Oncology, vol. 17: 813-817, 2006.

Yu et al., "Priming of naive T cells inside tumors leads to eradication of established tumors," Nature Immunology, vol. 5, No. 2: 141-149, 2004.

Zhang et al., "Generation of effective vaccines against liver cancer by using photodynamic therapy," Lasers Med Sci: 4pp., 2008.

Zwierzina, H., "Combining immunotherapy with classical anticancer therapy," Annals of Oncology, vol. 19, Supplement 7: vii252-vii255, 2008.

Unknown, "A Phase 3 Study of Talaporfin Sodium and Interstitial Light Emitting Diodes Treating Hepatocellular Carcinoma (HCC)," Study NCT00355355. 4pp., 2009.

Unknown, "Phase 3 Trial of LitxTM Plus Chemotherapy vs. Chemotherapy Only Treating Colorectal Cancer Patients With Recurrent Liver Metastatases," Study NCT00440310. 4pp., 2009.

* cited by examiner

ENHANCEMENT OF LIGHT ACTIVATED THERAPY BY IMMUNE AUGMENTATION USING ANTI-CTLA-4 ANTIBODY

RELATED APPLICATIONS

This application is a continuation of patent application Ser. No. 12/537,139, filed on Aug. 6, 2009, which issued on Aug. 9, 2011 as U.S. Pat. No. 7,993,640 and itself is based on provisional application Ser. No. 61/086,597, filed on Aug. 6, 2008, the benefits of the filing dates of which are hereby claimed under 35 U.S.C. §119(e) and 35 U.S.C. §120.

BACKGROUND

Abnormal cells in the body are known to selectively absorb certain dyes that have been perfused into a treatment site to a much greater extent than absorbed by surrounding tissue. For example, tumors of the pancreas and colon may absorb two to three times the volume of certain dyes, compared to normal cells. Once pre-sensitized by dye tagging in this manner, the cancerous or abnormal cells can be destroyed by irradiation with light of an appropriate wavelength or waveband corresponding to an absorbing wavelength or waveband of the dye, with minimal damage to surrounding normal tissue. Similarly, light activatable agents can be selectively administered to a specific treatment site, so that activation of such agents leads to tissue damage at the treatment site, but not surrounding tissue. Light activated drug therapy has been clinically used to treat metastatic breast cancer, bladder cancer, lung carcinomas, esophageal cancer, basal cell carcinoma, malignant melanoma, ocular tumors, head and neck cancers, and other types of malignant tissue growths. The light activated agent is either preferentially absorbed by the abnormal tissue, and/or is infused into vasculature that supplies the abnormal tissue, so that application of the light destroys the abnormal tissue. Because of the preferential drug absorption light activated drug therapy can kill malignant tissue with less effect on surrounding benign tissue than alternative treatment procedures.

Light is administered to an internal treatment site through an optical fiber from an external source such as a laser, or is applied to a site exposed during a surgical procedure, or is administered using an implantable probe. Several different embodiments of implantable light emitting probes for administering light activated therapy to an internal site within a patient's body are disclosed in commonly assigned U.S. Pat. No. 5,445,608. Further, a number of embodiments of flexible light emitting probes are disclosed in commonly assigned U.S. Pat. Nos. 5,800,478, 5,766,234, and 5,876,427. The above-referenced U.S. Pat. No. 5,445,608 teaches that an implantable probe containing a plurality of light sources can be transcutaneously introduced to a desired treatment site through a surgical incision and then left in place for an extended period of time so that the light emitted by light emitting diodes (LEDs) or other types of light sources mounted in the probe can administer light activated therapy to destroy abnormal tissue or other types of pathogenic organisms that have absorbed an appropriate photoreactive agent. Similarly, the flexible microcircuits disclosed in the above-noted patents are generally intended to be introduced into the body through a natural opening or through a small incision, and positioned at the treatment site using conventional endoscopic techniques. The flexibility of these microcircuits facilitates their insertion into the body and disposition at the treatment site. Additional light emitting probes are disclosed in commonly assigned U.S. Pat. No. 6,416,531, U.S. patent application Ser. No. 11/416,783, and U.S. patent application Ser. No. 12/445,061. It should be recognized that such implantable probes are exemplary, rather than limiting in regard to the concepts disclosed herein.

It has been recognized that synergistic effects can occur when different treatment methods are combined; however, successfully predicting such synergistic effects is rare.

It would be desirable to provide techniques for combining other treatment with light activated drug therapy treatment to achieve such a synergistic effect.

SUMMARY

In accord with the concepts disclosed herein, a method is defined for more effectively destroying abnormal tissue at one or more sites within a patient's body, to improve the efficacy of light activated therapy implemented at one or more such sites. In some embodiments, the beneficial therapeutic effect can extend to sites where abnormal tissue is present, and no light therapy has been implemented. Such a method can be used to treat metastatic diseases. The method includes the step of administering a light therapy treatment to at least one treatment site, to destroy a portion of the abnormal tissue at that treatment site. One or more immune system stimulating agents or factors is administered to the patient in association with the light therapy. In some embodiments, the immune system stimulating factor is administered to the patient after the light therapy, while in other embodiments the immune system stimulating factor is administered before the light therapy, or concurrently with the light therapy. It should be recognized that the concepts disclosed herein encompass combinations and permutations of the specifically disclosed embodiments.

Significantly, light therapy delivered to a first treatment site to destroy abnormal tissue has been linked with the destruction of abnormal tissue at other treatment sites that have not been exposed to light therapy. It is believed that the abnormal tissue destroyed by light therapy at the first treatment site releases certain factors (i.e., certain biological and chemical compounds) which naturally stimulate the patient's immune system. The stimulated immune system itself is then responsible for the destruction of abnormal tissue at other sites.

Administration of immune system stimulating factors (above and beyond factors released by abnormal tissue destroyed by the light therapy) can enhance the performance of light therapy in at least two ways.

First, in patients with suppressed immune systems, the stimulating factor released by the abnormal tissue destroyed by light therapy at the first treatment site may be insufficient to stimulate the patient's immune system to attack abnormal tissue at other treatment sites (i.e., treatment sites not exposed to light therapy). Administration of immune system stimulating factors in association with the light therapy will provide additional stimulus to the patient's immune system, such that the patient's immune system then attacks the abnormal tissue at treatment sites that have not been treated with light therapy.

Second, even in patients whose immune systems are healthy, the administration of immune system stimulating factors in association with the light therapy will provide additional stimulus to the patient's immune system, such that the patient's immune system then attacks the abnormal tissue at treatment sites that have not been treated with light therapy with greater vigor.

The concepts disclosed herein encompass the use of an antibody for cytotoxic T-lymphocyte antigen 4 (the anti-CTLA-4 antibody) to augment light therapy. In the context of the concepts disclosed herein, applicant hypothesizes that the anti-CTLA-4 antibody, when used in conjunction with light activated drug therapy, may produce synergistic effects, enhancing the treatment of abnormal tissues. Initial studies in animal models support such a hypothesis. Applicant further hypothesizes that when combined with light therapy at one or more treatment sites, an enhanced therapeutic result can be achieved using lower doses of the anti-CTLA-4 antibody than would be required in the absence of light therapy. For example, autoimmune side effects can occur when using anti-CTLA-4 antibodies, and the likelihood of such side effects occurring increases as the dose of anti-CTLA-4 antibodies increases. Thus, reducing the dose of anti-CTLA-4 antibodies will reduce the likelihood and/or intensity of such side effects. Indeed, applicant further hypothesizes that the problem of negative side effects of anti-CTLA-4 antibodies might only be overcome by combining it with light therapy to reduce a dose of anti-CTLA-4 antibodies required.

If desired, the light therapy can be provided once, or over a plurality of different times. The step of administering the light therapy treatment includes the step of administering a photoreactive agent to the treatment site. The photoreactive agent is selected for one or more characteristic wavebands of light absorption. Light having one or more emission wavebands substantially corresponding to at least one characteristic waveband of light absorption of the photoreactive agent is applied to the treatment site during each of the plurality of light therapy treatments. The light is absorbed by the photoreactive agent, which then destroys the abnormal tissue (either directly or by damaging vasculature providing nutrients to the abnormal tissue). Light can be administered from a light source implanted within the abnormal tissue, or disposed adjacent to the abnormal tissue.

The method may also include the step of imaging the treatment site to evaluate the effectiveness of the augmented light therapy treatment in destroying the abnormal tissue. Imaging may be accomplished using an ultrasound modality, a computer tomography modality, or a magnetic resonance imaging modality.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Figure 2:
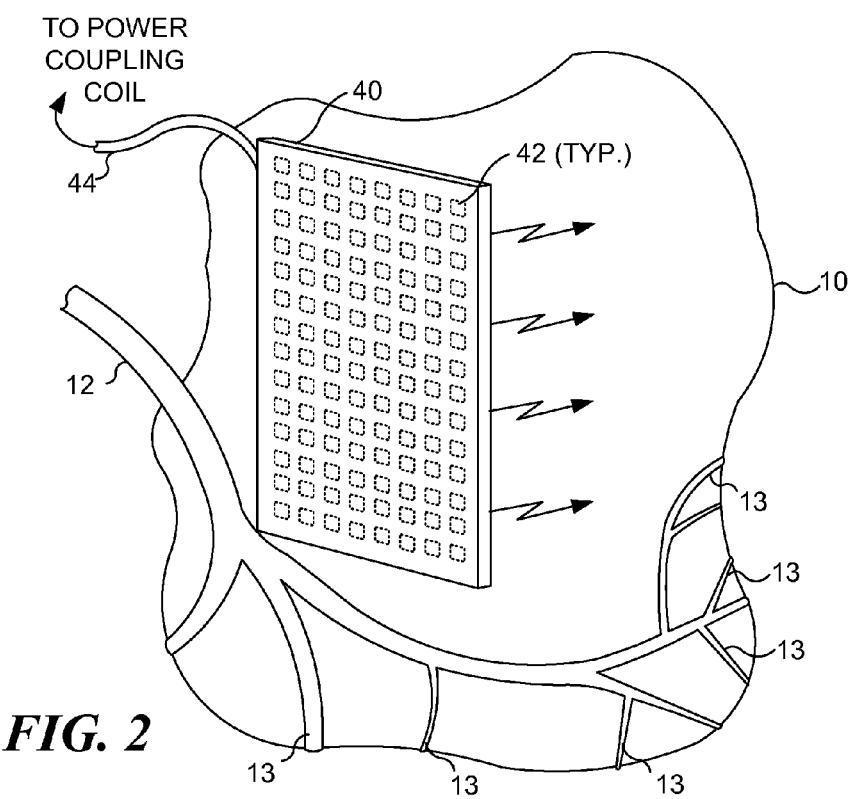

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 is a schematic illustration of a tumor, showing an implanted light source delivering a light activated therapy treatment internally to the tumor, where an immune-stimulating factor has been administered in association (i.e., either before, concurrently with, after, or a combination thereof) with light activated therapy; and FIG. 2 is a schematic illustration of a tumor, showing a light source delivering a light activated therapy treatment to an outer surface of the tumor, where an immune-stimulating factor has been administered in association (i.e., either before, concurrently with, after, or a combination thereof) with light activated therapy.

DESCRIPTION

Figures and Disclosed Embodiments Are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein. Further, it should be understood that any feature of one embodiment disclosed herein can be combined with one or more features of any other embodiment that is disclosed, unless otherwise indicated.

It is believed that damage to tumor cells resulting from administration of light activated therapy tends to attract macrophages that destroy the damaged tumor cells. Another aspect of the immunologic system relates to the response of the immunologic system to necrosis and apoptosis, for tissue destroyed by light activated therapy. Necrosis refers to the process in which cells release an inflammatory agent after they have been destroyed. Apoptosis refers to cells that do not release an inflammatory agent after being destroyed. The white cells, or neutrophils, in the body provide a scavenging function by clearing away both necrotic or apoptotic cells. It appears that abnormal tissue destroyed by light activated therapy releases factors that stimulate the patient's immune system, leading to systemic anti-tumor activity, as opposed to purely localized anti-tumor activity.

Thus, in a process in which light activated therapy treatment is delivered to a treatment site within a patient's body, the effectiveness of the systemic treatment can be extended by further stimulating the patient's immune system.

The method includes the step of administering a light therapy treatment to the treatment site, to destroy a portion of the abnormal tissue at the treatment site. One or more immune system stimulating agents or factors are administered to the patient in association with the light therapy. As noted above, the immune system stimulating factor (or factors, noting that such immune system boosters can be used individually or in combination) can be administered before the light therapy, concurrently with the light therapy, after the light therapy, or some combination thereof.

Administration of immune system stimulating factors (above and beyond factors released by abnormal tissue destroyed by the light therapy) can enhance the performance of light therapy in at least two ways.

In patients with suppressed immune systems, administration of immune system stimulating factors in association with the light therapy will provide additional stimulus to the patient's immune system, such that the patient's immune system then attacks the abnormal tissue at treatment sites that have not been treated with light therapy.

For such patients it may be beneficial to provide the immune enhancing factors prior to light therapy, such that the patient's own immune system can better respond to the factors released by the abnormal tissue destroyed by light therapy, thereby enhancing the systemic effect.

One technique for countering immune system suppression is to block negative regulators of the activation of T cells. One molecule that inhibits activation of such T cells is cytotoxic T-lymphocyte-associated antigen 4 (CTLA-4), which is expressed on activated T cells, where it appears to halt activation Inhibiting the activity of CTLA-4 would enable greater expansion of T-cell populations. Anti-CTLA-4 antibody has been developed to inhibit the immunosuppressive property of CTLA-4.

Administration of anti-CTLA-4 antibody in conjunction with light therapy should enhance the effectiveness of light therapy for the reasons noted above. The anti-CTLA-4 antibody can be administered before light therapy, or simultaneously with light therapy.

In a patient whose immune system is healthy, the administration of immune system stimulating factors (including anti-CTLA-4 antibody) in association with the light therapy will provide additional stimulus to the patient's immune system, such that the patient's immune system then attacks the abnormal tissue at treatment sites that have not been treated with light therapy with greater vigor. For such a patient, it may be more beneficial to provide the immune boosting agents concurrently with, or shortly after the light activated therapy.

As of June 2007, at least two fully human anti-CTLA-4 monoclonal antibodies have been developed; Tremelimumab™ (Pfizer), which is an IgG2, and Ipilimumab™ (Bristol-Myers Squibb), which is an IgG1. However, it must be emphasized that the concepts disclosed herein are not limited to any specific anti-CTLA-4 antibody.

Like most drugs, some side effects have been associated with the use of anti-CTLA-4 antibodies. Side effects have included rashes, diarrhea and hepatitis; and further side effects may be identified as anti-CTLA-4 antibody use becomes more common. Thus, one aspect of the concepts disclosed herein is the use of relatively smaller doses of anti-CTLA-4 antibodies (which will result in relatively fewer side effects) when anti-CTLA-4 antibodies are used in conjunction with light activated drug therapy. The phrase "relatively smaller doses of anti CTLA-4 antibodies" should be understood to mean doses 25% or less than doses of anti CTLA-4 antibodies used in clinical trials in the absence of light activated drug therapy. Applicant theorizes that relatively smaller doses of anti-CTLA-4 antibodies and light activated drug therapy may produce synergistic effects, such that anti-CTLA-4 antibodies can be used to stimulate the immune system with fewer side effects. Thus, one aspect of the concepts disclosed herein is combining anti-CTLA-4 antibody therapy with light therapy to reduce the side effects associated with anti-CTLA-4 antibody therapy alone by at least 25%.

Another aspect of the concepts disclosed herein is combining anti-CTLA-4 antibody therapy with light therapy to enable a standard dose of anti-CTLA-4 antibody to be reduced, where the standard dose corresponds to a dose used for therapy with anti-CTLA-4 antibodies alone.

In at least one exemplary, but not limiting embodiment, a sub-therapeutic dose of anti-CTLA-4 antibody is used in conjunction with light activated drug therapy. The term sub-therapeutic dose is intended to refer to a dose that, in the absence of light activated drug therapy, would not have a therapeutic effect.

In at least one embodiment, the light therapy is provided for an initial treatment of greater than about one hour. In some embodiments, the immune boosting factors can be provided for some time (i.e., a period of days) after the light therapy. Subsequent analysis of the treatment effectiveness may indicate that additional light activated therapy would be desirable. Thus, the method may also include the step of imaging the treatment site to evaluate an effectiveness of the augmented light therapy treatment in destroying the abnormal tissue. Imaging may be accomplished using an ultrasound modality, a computer tomography modality, or a magnetic resonance imaging modality.

It should be understood that the anti-CTLA-4 antibody can be administered before the light activated therapy, during the light activated therapy, or after the light activated therapy, or any combination and permutation thereof. In at least one embodiment, a plurality of light activated therapy treatments and anti-CTLA-4 antibody treatments can be administered in an alternating sequence. In another exemplary embodiment, a plurality of anti-CTLA-4 antibody treatments are administered after an initial light activated drug therapy treatment.

In general, the step of administering the light therapy treatment includes the step of administering a photoreactive agent to the treatment site. The photoreactive agent is selected for one or more characteristic wavebands of light absorption. Light having one or more emission wavebands substantially corresponding to at least one characteristic waveband of light absorption of the photoreactive agent is applied to the treatment site during each of the plurality of light therapy treatments. The light is absorbed by the photoreactive agent, which then destroys the abnormal tissue. Light can be administered from a light source implanted within the abnormal tissue, or disposed adjacent to the abnormal tissue.

As noted above, one aspect of the concepts disclosed herein is the use of the anti-CTLA-4 antibody to augment light therapy. If desired, one or more of the following additional different types of immune system stimulating factors can be administered, either individually or in combination. Such immune system "boosters" include Interleukin-2 (IL-2), Bacille Calmette-Guérin (BCG), Freund's adjuvant, other adjuvants, plasminogen activators such as streptokinase, tumor lysates, and anti cancer vaccines (such as Provenge™ and others). Various other agents useful in immunotherapy, such as mumps, candida, or trichophytin antigen, may also be of value in further stimulating the immune system in association with light therapy. As noted above, these agents can be used individually, or in various combinations and permutations. The anti-CTLA-4 antibody can also be used alone to augment light therapy.

In addition to enhancing systemic effects, other local (i.e., localized to the site treated with light activated therapy) advantages are believed likely to result from increasing neutrophil count after an initial light activated therapy treatment has destroyed some of the tumor cells at a treatment site. One potential advantage is that the removal of necrotic and apoptotic tissue by the increased number of neutrophils will likely reduce interstitial tumor pressure, thereby improving the delivery of drugs to the tumor site, particularly, the photoreactive agent employed for a successive light activated therapy treatment. In addition, the reduced interstitial tumor pressure will enhance the delivery of oxygen to the tumor, by increasing blood flow to the tumor. It is generally believed that singlet oxygen produced during a light activated therapy treatment is involved in the destruction of abnormal cells. The increase in oxygen delivery to a tumor will thus likely increase this desired action.

FIGS. 1 and 2 illustrate how the present invention is employed to achieve improved efficacy of one or more light activated therapy treatments delivered to a tumor 10. In FIG. 1, tumor 10 is supplied blood through one or more main vessels 12, having a plurality of branching vessels 13. Only one such branching vessel is illustrated to simplify the Figure. Because the cells comprising tumor 10 are abnormal, it tends to grow at a relatively rapid rate and if left unchecked, the condition may lead to a metastatic spread of the abnormal cells throughout a patient's body.

To administer light activated therapy treatments to tumor 10 in the example shown in FIG. 1, an elongate probe 20 is implanted internally within tumor 10 during a conventional surgical or endoscopic procedure. Probe 20 may be either rigid or flexible, as appropriate to the technique used to facilitate its placement within tumor 10 and depending upon the location of the tumor within the patient's body. Probe 20 includes a plurality of light sources 26, e.g., LEDs, which are disposed on opposite sides of a substrate 24. Details such as the electrically conductive traces that convey electrical current to each of the light sources are not shown. An optically transparent and biocompatible sheath 28 encloses light sources 26 and substrate 24, but allows light emitted by the light sources to be transmitted through to an interior surface 18 of the tumor.

In FIG. 1, a syringe 16 is illustrated; the syringe includes a needle 14 that is inserted into tumor 10 to infuse a photoreactive agent, such as porphyrin, into the treatment site. Alternatively, the photoreactive agent can be administered intravascularly. The photoreactive agent is selectively absorbed by the abnormal cells comprising tumor 10 to a much greater extent than by surrounding normal cells. Light emitted by light sources 26 has a characteristic waveband that is substantially equal to an absorption waveband of the photoreactive agent. Thus, tumor cells that have absorbed the photoreactive agent are destroyed by the light emitted from probe 20. In a related embodiment, the photoreactive agent is introduced into one or more blood vessels in the tumor, and the light from the light delivering probes activates the photoreactive agent in the blood vessels (note that such an embodiment does not require that the photoreactive agent be absorbed into the abnormal tissue).

After one or more light therapy treatments has been administered, syringe 16 is used to administer one or more of the above-identified immune stimulating factors (but not into the tumor as shown in FIG. 1) in multiple injections delivered over a period of time, to stimulate the patient's immune system. It should be recognized that the immune stimulating factor(s) can be administered using techniques other than injection, and some factors may require or work best using specific different methods of administering the factor. Thus, the specific technique employed to administer the factor is not limited to injection. The stimulated immune system results in systemic destruction of abnormal cells (i.e., beyond the portion of tumor 10 treated using light activated therapy).

FIG. 2 illustrates the use of a generally planar substrate probe 40 that includes a plurality of light sources 42, again preferably comprising LEDs. Light sources 42 are mounted on substrate 40 in a spaced-apart array that covers the surface of the substrate so that light emitted by the light sources is generally directed toward the outer surface of tumor 10. A biocompatible, optically transparent sheath (not shown) encloses the light sources and the conductive traces (also not shown) that convey electrical current to the light sources to energize them.

Syringe 16 (FIG. 1) is used for administering the photoreactive agent that selectively is absorbed by the abnormal cells comprising tumor 10 before the light is administered to the tumor from light sources 42. The light emitted by light sources 42 has a characteristic wavelength or waveband substantially corresponding to at least one absorption wavelength or waveband of the photoreactive agent preferentially absorbed by the abnormal cells and thus kills the abnormal cells without having significant effect on any normal cells of the surrounding tissue. In connection with at least an initial light activated therapy treatment that has then been delivered, killing some of the abnormal tumor cells, immune system stimulating factor (or factors) are administered (where it will be understood that such administration can occur before, concurrently with, and/or after the light activated therapy).

Although not shown in either Figure, it is also contemplated that an optical fiber can be used to administer light to a treatment site (e.g., tumor 10) within the patient's body from an external light source such as a laser. Other types of light sources can be used, either in connection with implanted probes like those shown in FIGS. 1 and 2, or to provide light from outside the patient's body. The only significant requirement is that the light source produces light having a characteristic waveband corresponding to a light absorption waveband of the photoreactive agent administered to the patient to implement the light activated therapy.

If an implanted probe is employed, electrical power can be supplied to energize the probe from outside the patient's body using an external power source that is connected to a coil applied on the outer surface of the patient's skin, generally opposite an internally implanted coil that is connected to the implanted probe (neither shown), for example, through a line 44 as illustrated in FIG. 2. A similar arrangement can be used to provide power and other signals to implanted probe 20, in FIG. 1.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A method for destroying cancerous tissue within a patient's body, comprising the steps of:
   (a) administering a light activated drug therapy treatment to the treatment site, the light activated drug therapy treatment destroying a portion of the cancerous tissue at the treatment site and releasing factors that stimulate the patient's immune system; and
   (b) administering an immune system stimulating factor to the patient in association with the light activated drug therapy treatment, said immune system stimulating factor and said light activated drug therapy together having a synergistic effect that systemically enhances destruction of cancerous tissue, even to cancerous tissue that itself has not been treated by the light activated drug therapy treatment, the immune system stimulating factor comprising an anti-CTLA-4 antibody, release of the factors that stimulate the patient's immune system caused by the light activated drug therapy enabling a lower dose of the anti-CTLA-4 antibody to be used than is normally used when administered without also administering the light activated drug therapy.

2. The method of claim 1, wherein the anti-CTLA-4 antibody is administered using a dose that is smaller than would be required to achieve a beneficial therapeutic effect in the absence of administering light therapy treatment.

3. The method of claim 1, wherein the anti-CTLA-4 antibody is administered using a dose that causes minimal side effects.

4. The method of claim 1, wherein the anti-CTLA-4 antibody is administered using a reduced dose that significantly reduces side effects compared to a standard dose which is administered in the absence of administering light therapy treatment.

5. The method of claim 1, wherein the anti-CTLA-4 antibody is administered using a sub-therapeutic dose.

6. The method of claim 1, wherein the anti-CTLA-4 antibody is administered before administering light therapy treatment.

7. The method of claim 1, wherein the anti-CTLA-4 antibody is administered after administering light therapy treatment.

8. The method of claim 1, wherein the anti-CTLA-4 antibody is administered while administering light therapy treatment.

\* \* \* \* \*